United States Patent [19]
Mase et al.

[11] Patent Number: 4,585,499
[45] Date of Patent: Apr. 29, 1986

[54] METHOD OF PRODUCING CERAMICS

[75] Inventors: Syunzo Mase, Ama; Shigeo Soejima, Nagoya, both of Japan

[73] Assignee: NGK Insulators, Ltd., Japan

[21] Appl. No.: 636,359

[22] Filed: Jul. 31, 1984

[30] Foreign Application Priority Data

Aug. 9, 1983 [JP] Japan .................................. 58-144476

[51] Int. Cl.⁴ ...................... B32B 18/00; B32B 31/26; C04B 37/02
[52] U.S. Cl. ................................. 156/89; 204/425; 204/426; 204/427; 204/429; 501/102; 501/103; 501/104
[58] Field of Search ................... 156/89; 204/425, 426, 204/427, 429; 501/102, 103, 104

[56] References Cited

U.S. PATENT DOCUMENTS

| 4,266,979 | 5/1981 | Miyoshi et al. | 501/103 |
| 4,334,940 | 6/1982 | Habdas et al. | 156/89 |
| 4,505,806 | 3/1985 | Yamada | 156/89 |
| 4,505,807 | 3/1985 | Yamada | 156/89 |
| 4,507,394 | 3/1985 | Mase et al. | 501/103 |

Primary Examiner—Caleb Weston
Attorney, Agent, or Firm—Parkhurst & Oliff

[57] ABSTRACT

Zirconia powder is formed by dry grinding, and slurry of the zirconia powder with nonaqueous solvent is shaped and fired.

15 Claims, 4 Drawing Figures

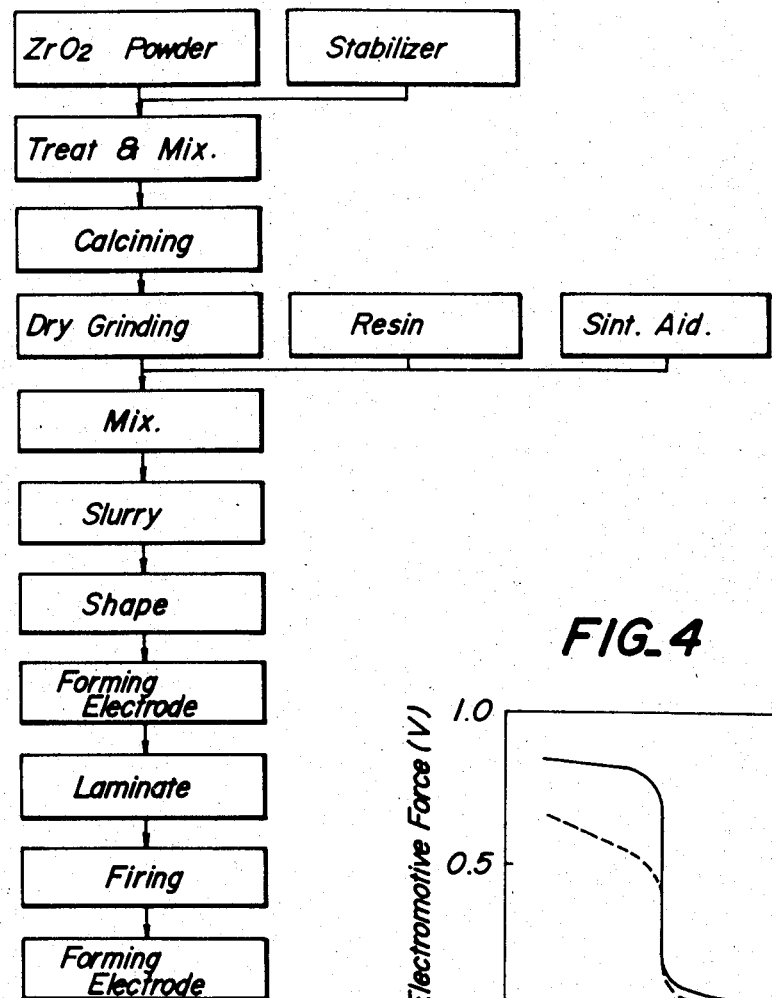

METHOD OF PRODUCING CERAMICS

BACKGROUND OF THE INVENTION

1. Field of the Invention

This invention relates to a method of producing ceramics which can be sintered at a low temperature and have a high moldability, and more particularly to a method of producing zirconia ceramics of the above type.

2. Description of the Prior Art

Methods of producing zirconia ceramics according to the prior art use zirconia powder made by wet grinding, resulting in the following shortcomings. Namely, with the wet ground zirconia powder, high sintering temperature in excess of 1,500° C. are necessary, so that various difficulties associated with the high sintering temperature, such as a very low energy efficiency and a low mechnical strength due to large grain growth at the high sintering temperature, results.

To reduce the sintering temperature, a method of using zirconia powder having a small grain size has been proposed, but this method has shortcomings of the low moldability of the zirconia powder and the large shrinkage which occurs during sintering. There have not been any methods which meet the requirement of both high moldability and the low sintering temperature.

FIG. 1 shows a typical laminated oxygen sensor, which comprises a metallic layer 1 for a first electrode, hereinafter called "first electrode", a solid electrolyte layer 2, a substrate 3, and a metallic layer 4 for a second electrode; hereinafter called "second electrode". In a typical method of the prior art for producing the laminated structure of FIG. 1, the solid electrolyte layer 2 is formed by using a prefiring zirconia layer made of a slurry containing wet ground zirconia powder, and the first electrode 1 is formed by using an electrode layer mainly consisting of electron-conductive metallic powder.

The green zirconia layer 2 is overlaid on the substrate 3 while inserting the electrode layer therebetween, which substrate 3 is either a green layer made of ceramics material or a fired layer. After firing them into an unitary body, the second electrode 4 is formed on the solid electrolyte layer 2 by a physical method such as evaporation or a manual method such as brushing. Such method of the prior art has a shortcoming in that the sintering temperature of the green zirconia layer made of wet ground zirconia powder is high, being higher than 1,500° C., so that the metallic particles of the first electrode 1 grow too large, resulting in a considerable reduction of the activity of the electrode.

To overcome this shortcoming, another method of the prior art reduces the grain size of the zirconia powder in the green zirconia layer for the solid electrolyte layer 2 by using wet grinding, so as to reduce the sintering temperature of the green zirconia layer. However, such method also has a shortcoming in that, the small grain size achieved by the wet grinding tends to cause cracks and pinholes in the green zirconia layer, and such cracks and pinholes remain even after the sintering of zirconia layer, and a solid electrolyte layer of sound and dense structure cannot be obtained.

SUMMARY OF THE INVENTION

Therefore, the present invention intends to obviate the above-mentioned shortcomings of the conventional methods of producing ceramics.

A first object of the invention is to establish a new method of producing zirconia ceramics which enables sintering at a low temperature with a small amount of shrinkage during sintering.

A second object of the invention is to establish a new method of producing ceramics which provides a highly active metal layer and a fully sintered zirconia layer even if a metal-forming layer and a green zirconia layer are fired together.

A third object of the invention is to establish a method of producing ceramics which are free from cracks and pinholes both in the green zirconia layer formed from a slurry and in the zirconia layer sintered at a low temperature.

Essentially, a method of producing ceramics according to the present invention comprises steps of preparing powder consisting essentially of zirconia by dry grinding, making a nonaqueous slurry of the thus dry ground powder, treating the slurry into a shaped body, and firing the shaped body at a temperature higher than 1,100° C.

What is meant by "dry grinding" here refers to grinding without addition of fluid in an amount sufficient to result in fluidity of the powder during the grinding.

In a preferred embodiment of the invention, the powder material to be dry ground may contain 70-98 mol % of zirconia and 2-30 mol % of at least one stabilizer selected from the group consisting of yttria ($Y_2O_3$), ytterbium oxide ($Yb_2O_3$), scandium oxide ($Sc_2O_3$), neodymium oxide ($Nd_2O_3$), samarium oxide ($Sm_2O_3$), calcia (CaO), and magnesia (MgO). The dry ground powder material consisting essentially of zirconia, preferably has a specific surface area of larger than 5 $m^2/g$. A slurry is made by mixing the dry ground powder material with the a nonaqueous solvent, preferably with addition of resin.

A green zirconia layer is formed by treating the nonaqueous slurry, and a paste layer is applied at least on one side surface of the green zirconia layer by using a paste mainly consisting of metallic powder or a compound capable of producing metal upon heating. The green zirconia layer is overlaid on a fired or green layer consisting of zirconia or an insulating material, while placing the paste layer therebetween, so as to form a laminated body. Desired ceramics are produced by firing the laminated body at a temperature higher than 1,100° C.

In another embodiment of the invention, an oxygen sensor element is produced by preparing a fired or green substrate made of zirconia or an insulating material, applying a green first electrode layer or a fired first electrode on the substrate, the green first electrode layer mainly consisting of metal powder or a compound capable of producing metal upon heating, overlaying the substrate on the above-mentioned green zirconia layer so as to form a laminated body, firing the laminated body at a temperature higher than 1,100° C. so as to produce a zirconia ceramic, and forming a second electrode on a surface of the zirconia ceramic which is electrically connected to the first electrode.

A further embodiment of the invention is a method to produce an oxygen sensor element, which method comprises steps of preparing a fired or green substrate consisting of zirconia or an insulating material, preparing a first electrode layer and a second electrode layer consisting of metallic powder or a compound capable of producing metal upon heating, overlaying or stacking the substrate, the first electrode layer, the second electrode layer, and the above-mentioned green zirconia layer so as to form a laminated body while placing the first electrode layer and the second electrode layer on opposite surfaces of the green zirconia layer, and firing the laminated body at a temperature higher than 1,100° C.

BRIEF DESCRIPTION OF THE DRAWINGS

For a better understanding of the invention, reference is made to the accompanying drawings, in which:

FIG. 3 is a flow chart of a process of forming a laminated structure in accordance with the method of the invention; and FIG. 4 shows the electromotive force versus air fuel ratio curves, for an oxygen sensor element made by a method of the invention and a conventional element.

In FIG. 1 and FIG. 2, numerals 1, 11 are first eletrode layers or first electrodes, 2, 12 are solid electrolyte layers, 3, 13 are substrates, and 4, 14 are second electrode layers or second electrodes.

DESCRIPTION OF THE PREFERRED EMBODIMENTS

Figure 1:
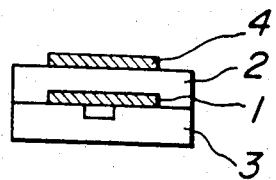
FIG. 1 is an explanatory diagram of a laminated structure formed by a conventional ceramics producing method.
Figure 2:
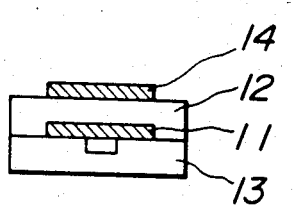
FIG. 2 is an explanatory diagram of a laminated structure formed by a method according to the present invention.

As a preferred embodiment of the invention, a method of producing an oxygen sensor element will be described. At a certain step of the method of this embodiment, a laminated structure or body is formed as shown in FIG. 2. In the figure, a first electrode layer 11 is formed on one side surface of a solid electrolyte layer 12. A substrate 13 adheres to the solid electrolyte layer 12 with the first electrode layer 11 disposed therebetween. A second electrode layer 14 is formed on the opposite side surface of the solid electrolyte layer 12. In the following, the numeral 11 may also represent a first electrode itself, while the numeral 14 may also represent a second electrode itself.

As a first feature of the invention, the laminated body as shown in FIG. 2 can be sintered at a low temperature with a small amount of shrinkage occurring during sintering. A second feature of the invention is in that the activity of the electrode, e.g., the first electrode 11 and/or the second electrode 14 of FIG. 2, can be kept high even if such electrode of its green layer is fired together with a green layer of the solid electrolyte layer 12. Especially, the high activity of the first eletrode 11 can be maintained even after firing it together with the green zirconia layer for the solid electrolyte layer 12, because the sintering temperature of the green zirconia in the solid electrolyte layer 12 used in the method of the invention is low.

As a third feature of the invention, the solid electrolyte layer 12 is substantially free from cracks and pinholes despite the low sintering temperature thereof. If the sintering temperature of the solid electrolyte such as zirconia ceramics is reduced by using wet pulverized fine zirconia powder, moldability of the zirconia porcelain is low even at a green stage because of the occurrence of cracks and pinholes therein. The inventors have succeeded in reducing the sintering temperature while maintaining a high moldability. To this end, the method of the invention prepares the fine zirconia powder by dry grinding.

Preferably, the specific surface area of the dry pulverized zirconia powder is more than 5 $m^2/g$, and a green body of the solid electrolyte is formed by using a nonaqueous slurry of such zirconia powder.

The method of the invention will be described in detail now by referring to FIG. 3 showing a flow chart of a process of making the laminated ware of FIG. 2 as an embodiment of the invention. A powder material is prepared by mixing 70–98 mol % of zirconia powder and 2–30 mol %, in terms of the total of converted oxides, of at least one stabilizer selected from the group consisting of oxides of rare earth elements such as yttria ($Y_2O_3$), ytterbium oxide ($Yb_2O_3$), scandium oxide ($Sc_2O_3$), neodymium oxide ($Nd_2O_3$), and samarium oxide ($Sm_2O_3$), other oxides such as calcia (CaO) and magnesia (MgO), and compounds capable of producing any of the preceding oxides upon heating. Less than 30 parts by weight of at least one sintering aid selected from the group consisting of silica, alumina, clay, and the like may be added to 100 parts by weight of the powder material thus mixed.

The powder material is thoroughly mixed in a ball mill under wet or dry conditions. Preferably, the mixed powder material is calcined at 200°–1,200° C. for 1–10 hours. Further, the calcined mixture is finely ground by a dry grinding process. The specific surface area of the thus dry ground powder is preferably larger than 5 $m^2/g$.

The dry grinding is carried out without addition of fluid in an amount sufficient for rendering fluidity to the powder during the grinding. Preferably, a grinding aid, such as polyethylene glycol stearate, oleic acid, or the like, may be added in the powder during the dry grinding. The grinding aid prevents the powder from aggregating so as to ensure effective pulverization.

Preferably, less than 60% by volume of resin such as polyvinyl butyral, methyl methacrylate, ethyl cellulose, or the like, and more preferably together with a plasticizer such as dioctyl phthalate or the like, is added to the dry ground powder. A nonaqueous slurry is made by mixing the dry ground powder with a nonaqueous solvent such as trichloroethylene, butyl alcohol, diethylene glycol monobutylether, toluene, methyl ethyl ketone, tetralin, terpineol, 2-ethyl hexyl alcohol, butyl acetate, xylene, or the like.

The nonaqueous slurry is formed into a layer by using a doctor blade or the like, and a green zirconia layer is made by drying the thus treated layer at a temperature preferably above room temperature but not higher than 200° C. An electrode layer is applied onto one side surface of the green zirconia layer, for instance, by screen printing of a paste mainly consisting of electron-conductive metallic powder such as powder of platinum, phodium, gold, or the like, or a compound capable of generating such metal upon heating.

The green zirconia layer with the electrode layer is overlaid either on another green zirconia layer or on a green insulating material layer, while placing the electrode layer therebetween, so as to form a laminated body. The laminated body is fired at a temperature higher than 1,100° C., preferably 1,200°–1,400° C., and the first electrode 11, the solid electrolyte layer 12, and the substrate 13 are formed as shown in FIG. 2. Then, the second electrode 14 is formed on the opposite side surface of the solid electrolyte layer 12 by applying a paste layer, for instance, through screen printing of a paste mainly consisting of electron-conductive metal or a compound capable of generating such metal upon heating, and firing the paste layer.

The second electrode 14 may be formed by any other suitable method, such as sputtering, ion plating, evaporating, and the like.

Instead of the sequence of steps as illustrated in FIG. 3, the following sequence of steps may be used without departing from the scope of the invention. Namely, a non-aqueous slurry of powder material mainly consisting of dry pulverized zirconia is prepared in the manner described above. An electrode layer is applied to one side surface of a fired or green substrate mainly consisting of substrate-forming ceramics material, for instance, by screen printing of a paste mainly consisting of electron-conductive metallic powder or a compound capable of generating such metal upon heating.

After the paste of the electrode layer is dried, a green zirconia layer is formed on that side surface of the substrate so as to cover the electrode layer, for instance, by screen printing of the above-mentioned nonaqueous slurry, so as to form a laminated body. After being dried, the laminated body is fired at a temperature above 1,100° C., preferably 1,200°–1,400° C., so as to produce the first electrode 11, the solid electrolyte layer 12, and the substrate 13, as shown in FIG. 2. The second electrode 14 is formed thereon in the same manner as described above.

In the above-described processes according to the method of the invention, the first electrode 11 and the solid electrolyte layer 12 are formed simultaneously. However, they can be formed in succession. The second electrode 14 may be formed and fired simultaneously with the formation and firing of the first electrode 11 and the solid electrolyte layer 12. The stabilizer and the sintering aid may be added at any step before the nonaqueous slurry is made in the method of the invention. The green layer consisting of ceramic material to be used in the method of the invention may be in the form of a separate laminar plate or a layer overlaid or printed on another substrate.

The reason why the dry ground zirconia powder and the nonaqueous solvent are used in the method of the invention to obviate the shortcomings of the prior art will be summarized next.

The surface of zirconia powder particles have a very high affinity with water. Especially, when fine powder particles of zirconia with a specific surface area in the order of less than 5 $m^2/g$ are formed in water, it is difficult to produce a slurry with good dispersion even if a nonaqueous solvent is added later, because of the presence of adsorption water layer formed on the surface of the zirconia particle by adsorption and the formation of strong aggregate particles. When such slurry with the insufficient dispersion is dried, the shrinkage at the time of drying tends to cause cracks and relatively inferior sinterability of particles.

On the other hand, the method of the invention uses dry grinding for making fine particles of zirconia and nonaqueous solvent for making a nonaqeuous slurry, possibly with a binder, so that the zirconia particles are prevented from adsorbing water during the pulverization and mixing in the slurry. Thus, a good dispersion is obtained in the nonaqueous slurry, so that the high sinterability of the zirconia particles made by dry grinding is maintained in the shaped body. The invention is based on the inventors' finding of the above fact.

The reason for firing the green zirconia layer or body at a temperature above 1,100° C. in the method of the invention is in that, if the firing temperature is below 1,100° C., sufficient sintering of the ceramics cannot be effected. Preferably, the firing is effected at 1,200°–1,400° C., so as to produce ceramics of optimal quality and highly active metallic layers.

When the specific surface area of the dry ground zirconia powder is more than 5 $m^2/g$, the sintering temperature can be easily reduced to a sufficiently low level for the purpose of the invention and a high moldability can be achieved. In the nonaqueous slurry to be used in the method of the invention, more than 2 mol % of a stabilizer is preferable, because it improves the durability of the ceramics. However, good mechanical strength cannot be achieved if the amount of the stabilizer exceeds 30 mol %.

The invention will be described in further detail by referring to examples.

EXAMPLE 1

Powder material was prepared by mixing 500 g of zirconia powder having a specific surface area of 5 $m^2/g$ and yttrium nitrate, as a stabilizer, at a rate in terms of a $Y_2O_3/ZrO_2$ mol ratio of 4/96. After mixing in a ball mill, the powder material was calcined at 900° C. for 2 hours. The calcined material was coarsely ground by a roll crusher. A mixture containing 99 parts by weight of the thus ground coarse powder particles, 1 part by weight of clay as a sintering aid, and 0.5 part by weight of polyethylene glycol stearate as a grinding aid was subjected to dry grinding by a ball mill for 24 hours. The powder material after the dry grinding had a specific surface area of 8 $m^2/g$.

A nonaqueous slurry with a viscosity of 600 poise was made by mixing 100 parts by weight of the thus dry pulverized zirconia powder material, 8 parts by weight of polyvinyl butyral, and 100 parts by weight of trichloroethylene in a ball mill for 16 hours. The thus prepared slurry was treated into a 0.8 mm thick planar body by using a doctor blade, and a 0.6 mm thick green zirconia layer was obtained by drying the planar body at 50° C. for 12 hours. A rectangular green zirconia layer of 10 mm width and 40 mm length was cut out from the thus dried zirconia layer.

A platinum paste was screen printed on one side surface of the rectangular green zirconia layer, and dried at 100° C. for 10 minutes. Another green zirconia layer with the identical chemical composition was overlaid on the rectangular green zirconia layer while placing the platinum paste layer therebetween, so as to form a laminated body. The laminated body was fired at 1,350° C. for 3 hours, and a first electrode 11, a solid electrolyte layer 12, and a substrate 13 as shown in FIG. 2 were obtained. Then, a 1 $\mu$m thick second platinum electrode 14 was formed on the opposite side surface of the solid electrolyte layer 12 to the first electrode 11 by sputtering. Whereby, an oxygen sensor element of laminated type was produced.

The electromotive force versus air fuel ratio characteristics of the oxygen sensor element of laminated type thus produced was measured at 400° C., and the measured values are shown in FIG. 4 by the solid line curve. For the sake of reference, the electromotive force versus air fuel ratio characteristics of a conventional oxygen sensor element of laminated type at 400° C. was measured, which is shown by the dashed line curve in FIG. 4. The conventional oxygen sensor element was prepared in the same manner as the above-mentioned example of the invention except that wet ground zirconia powder was used instead of the above-mentioned dry ground zirconia powder and that the firing was effected at 1,500° C. for 3 hours.

As can be seen from FIG. 4, the conventional oxygen sensor element using the wet ground zirconia powder has a lower electromotive force than that of the example of the invention, because the activity of the conventional sensor element is lower than that of the example of the invention. In other words, the excellent activity and sufficient electromotive force of the oxygen sensor element produced by the method according to the present invention were proven by the above example.

EXAMPLE 2

A green zirconia planar body was prepared in the same manner as that of the preceding Example 1, and it was fired at 1,350° C. for 3 hours to form a fired zirconia layer. A layer of platinum paste was applied to one side surface of the fired zirconia layer by screen printing. After being dried at 150° C. for 15 minutes, the platinum paste layer was baked at 1,000° C. for 10 minutes, so as to form a platinum electrode. The nonqeuous zirconia slurry prepared in Example 1 was screen printed on the fired zirconia layer so as to cover the platinum electrode, and a homogeneous green zirconia layer without any cracks was produced by drying the thus printed slurry layer at 100° C. for 10 minutes. The green zirconia layer thus formed was fired together with the fired zirconia layer at 1,350° C. for 3 hours, and a 1 μm thick platinum electrode was sputtered on the thus fired zirconia layer so as to face the first formed electrode. Whereby, an oxygen sensor element of the laminated type as shown in FIG. 2 was produced.

The solid electrolyte layer 12 of the thus produced oxygen sensor element proved to be sound and densely sintered. The electromotive force of this Example was found to be not inferior to that of Example 1.

As described in the foregoing, with a method of producing a ceramics according to the present invention, zirconia ceramics can be sintered at a low temperature with a small amount of shrinkage occurring during sintering, so that, firstly, a green metallic layer can be fired together with a green zirconia layer while maintaining a high activity of the metallic layer, and secondary, a green zirconia layer with a high moldability can be formed by using a nonaqueous slurry of dry ground zirconia powder. Thus, a laminated structure having a zirconia layer and a metallic layer can be sintered into a unitary ware while maintaining the high activity of the metallic layer without causing any defects such as cracks and pinholes in the sintered zirconia layer.

Therefore, the method of producing ceramics according to the invention is suitable not only for manufacturing the illustrated oxygen sensor element, but also for making other articles utilizing the excellent moldability and the low sintering temperature with a low shrinkage of zirconia, such as cutting tools, machine parts, and the like.

Although the invention has been described with a certain degree of particularity, it is understood that the present disclosure has been made only by way of example and that numerous changes in details of construction and the combination and arrangement of parts as well as sequence of steps may be resorted to without departing from the scope of the invention as hereinafter claimed.

What is claimed is:

1. A method of producing ceramics comprising the steps of:
   preparing a powder consisting essentially of zirconia;
   calcining said powder at a temperature of 200°–1,200° C. for at least one hour;
   dry grinding said powder
   forming a non-aqueous slurry of the dry ground powder;
   shaping said non-aqueous slurry into a body; and
   firing the shaped body at a temperature greater than 1,100° C.

2. The method of claim 1, wherein a layer of paste containing metallic powder is overlaid on at least one side surface of said shaped body and the shaped body is then fired.

3. The method of claim 1, wherein a layer of paste containing a compound capable of forming metal upon heating is overlaid on at least one side surface of said shaped body and the shaped body is then fired.

4. The method of claim 1, wherein a layer of paste containing metallic powder is overlaid on at least one side surface of said shaped body, and said shaped body is overlaid on a green layer consisting essentially of a ceramic material, thereby forming a laminated body, and the laminated body is fired into a unitary body.

5. The method of claim 1, wherein a layer of paste containing metallic powder is overlaid on at least one side surface of said shaped body, and the shaped body is overlaid on a fired layer consisting essentially of a ceramic material, thereby forming a laminated body, and the laminated body is fired into a unitary body.

6. The method of claim 1, wherein a layer of paste containing a compound capable of forming metal upon heating is overlaid on at least one side surface of said shaped body, the shaped body is overlaid on a green layer consisting essentially of a ceramic material, thereby forming a laminated body, and the laminated body is fired into a unitary body.

7. The method of claim 1, wherein a layer of paste containing a compound capable of producing metal upon heating is overlaid on at least one side surface of said shaped body, and the shaped body having the layer of paste is overlaid on a fired layer consisting essentially of a ceramic material, thereby forming a laminated body, and the laminated body is fired into a unitary body.

8. The method of producing ceramics of claim 1, wherein said dry ground powder has a specific surface area of greater than 5 m$^2$/g.

9. A method of producing an oxygen sensor element comprising the steps of:
   preparing a substrate consisting essentially of a ceramic material;
   overlaying a first electrode layer on said substrate, said first electrode layer consisting essentially of at least one material selected from the group of materials consisting of metallic powder and a compound capable of forming metal upon heating;
   heating said substrate with the first electrode layer thereon to form a first electrode;
   overlaying said heated substrate on a shaped body to form a laminated body, said shaped body being formed by:
   preparing a powder consisting essentially of zirconia;

calcining said powder at a temperature of 200–1,200° C. for at least one hour;
dry grinding said powder;
forming a non-aqueous slurry of the dry ground powder; and
shaping said non-aqueous slurry into a body;
firing said laminated body at a temperature greater than 1,100° C. to produce a zirconia ceramic body; and
forming a second electrode on said zirconia ceramic body to form an oxygen sensor element.

10. The method of producing an oxygen sensor element of claim 9, wherein said dry ground powder has a specific surface area of greater than 5 m²/g.

11. A method of producing an oxygen sensor element comprising the steps of:
preparing a substrate consisting essentially of a zirconia ceramic material;
overlaying a first electrode layer on said substrate, said first electrode layer consisting essentially of at least one material selected from the group of materials consisting of metallic powder and a compound capable of forming metal upon heating;
heating said substrate with the first electrode layer thereon to form a first electrode;
overlaying said heated substrate on a shaped body to form a laminated body, said shaped body being formed by:
preparing a powder consisting essentially of zirconia;
calcining said powder at a temperature of 200°–1,200° C. for at least one hour;
dry grinding said powder;
forming a non-aqueous slurry of the dry ground powder; and
shaping said non-aqueous slurry into a body;
firing said laminated body at a temperature greater than 1,100° C. to produce a zirconia ceramic body; and
forming a second electrode on said zirconia ceramic body to form an oxygen sensor element.

12. A method of producing an oxygen sensor element comprising the steps of:
preparing a substrate consisting essentially of a ceramic material;
preparing a first electrode layer on said substrate, said first electrode layer consisting essentially of at least one material selected from the group of materials consisting of metallic powder and a compound capable of forming metal upon heating;
overlaying said substrate and said first electrode layer on a shaped body to form a laminated body, said shaped body being formed by:
preparing a powder consisting essentially of zirconia;
calcining said powder at a temperature of 200°–1,200° C. for at least one hour;
dry grinding said powder;
forming a non-aqueous slurry of the dry ground powder; and
shaping said non-aqueous slurry into a body;
firing said laminated body at a temperature greater than 1,100° C. to produce a zirconia ceramic body with a first electrode therein; and
forming a second electrode on said zirconia ceramic body to form an oxygen sensor element.

13. A method of producing an oxygen sensor element comprising the steps of:
preparing a substrate consisting essentially of a zirconia ceramic material;
preparing a first electrode layer on said substrate, said first electrode layer consisting essentially of at least one material selected from the group of materials consisting of metallic powder and a compound capable of forming metal upon heating;
overlaying said substrate and said first electrode layer on a shaped body to form a laminated body, said shaped body being formed by:
preparing a powder consisting essentially of zirconia;
calcining said powder at a temperature of 200°–1,200° C. for at least one hour;
dry grinding said powder;
forming a non-aqueous slurry of the dry ground powder; and
shaping said non-aqueous slurry into a body;
firing said laminated body at a temperature greater than 1,100° C. to produce a zirconia ceramic body with a first electrode therein; and
forming a second electrode on said zirconia ceramic body to form an oxygen sensor element.

14. A method of producing an oxygen sensor element comprising the steps of:
preparing a substrate consisting essentially of a ceramic material;
preparing a first eletrode layer and a second electrode layer, said electrode layers consisting essentially of at least one material selected from the group of materials consisting of metallic powder and a compound capable of forming metal upon heating;
preparing a green zirconia layer by:
preparing a powder consisting essentially of zirconia;
calcining said powder at a temperature of 200°–1,200° C. for at least one hour;
dry grinding said powder;
forming a non-aqueous slurry of the dry ground powder; and
shaping said non-aqueous slurry into a green zirconia layer;
overlaying said substrate, said first and second electrode layer and said green zirconia layer to form a laminated body with said zirconia layer being between said first and second electrodes; and
firing said laminated body at a temperature greater than 1,100° C. to produce an oxygen sensor element.

15. A method of producing an oxygen sensor element comprising the steps of:
preparing a substrate consisting essentially of a zirconia ceramic material;
preparing a first electrode layer and a second electrode layer, said electrode layers consisting essentially of at least one material selected from the group of materials consisting of metallic powder and a compound capable of forming metal upon heating;
preparing a green zirconia layer by:
preparing a powder consisting essentially of zirconia;
calcining said powder at a temperature of 200°–1,200° C. for at least one hour;
dry grinding said powder;
forming a non-aqueous slurry of the dry ground powder; and shaping said non-aqueous slurry into a green zirconia layer;

overlaying said substrate, said first and second electrode layers and said green zirconia layer to form a laminated body with said zirconia layer being between said first and second electrodes; and firing said laminated body at a temperature greater than 1,100° C. to form an oxygen sensor element.

* * * * *